United States Patent
Nagy et al.

(10) Patent No.: US 11,622,684 B2
(45) Date of Patent: Apr. 11, 2023

(54) PHYSIOLOGICAL MONITORING SYSTEM

(71) Applicant: Endotronix, Inc., Lisle, IL (US)

(72) Inventors: Michael Nagy, Lombard, IL (US);
Harry Rowland, Plainfield, IL (US);
Ariel Johnson, Chicago, IL (US); Brett Quas, Pewaukee, WI (US)

(73) Assignee: ENDOTRONIX, INC., Lisle, IL (US)

( * ) Notice: Subject to any disclaimer, the term of this patent is extended or adjusted under 35 U.S.C. 154(b) by 473 days.

(21) Appl. No.: 16/040,034

(22) Filed: Jul. 19, 2018

(65) Prior Publication Data

US 2019/0021597 A1    Jan. 24, 2019

Related U.S. Application Data

(60) Provisional application No. 62/534,261, filed on Jul. 19, 2017.

(51) Int. Cl.
*A61B 5/02* (2006.01)
*A61B 5/00* (2006.01)
(Continued)

(52) U.S. Cl.
CPC .......... *A61B 5/0022* (2013.01); *A61B 5/0006* (2013.01); *A61B 5/1455* (2013.01);
(Continued)

(58) Field of Classification Search
None
See application file for complete search history.

(56) References Cited

U.S. PATENT DOCUMENTS

| 3,714,595 A | 1/1973 | Denenberg et al. |
| 3,872,455 A | 3/1975 | Fuller et al. |
| (Continued) | | |

FOREIGN PATENT DOCUMENTS

| CA | 2840645 | 1/2013 |
| CN | 1701464 | 11/2005 |
| (Continued) | | |

OTHER PUBLICATIONS

International Search Report and Written Opinion of the International Searching Authority for PCT/US2017/042702 dated Apr. 3, 2018, 17 pages.

(Continued)

*Primary Examiner* — Kennedy Schaetzle
(74) *Attorney, Agent, or Firm* — McDonald Hopkins LLC

(57) ABSTRACT

Disclosed is a physiologic monitoring system comprising a central hub in communication with a management portal for communicating physiologic measurements taken from a plurality of peripheral devices on a patient. At least one non-invasive peripheral device may measure physiologic data from a patient and be in communication with said central hub. A system including an invasive peripheral device may be associated with said patient and be in communication with said central hub. The central hub may be scalable to collect and communicate measurements from the non-invasive peripheral device and the invasive peripheral device. The at least one non-invasive peripheral device may include a blood pressure cuff, an oxygen sensor, a weight scale, and an ECG monitor. The invasive peripheral device may include a wireless sensor reader that may be adapted to measure physiologic data from a sensor implant placed within the cardiovascular system of said patient.

18 Claims, 8 Drawing Sheets

(51) Int. Cl.

| | | |
|---|---|---|
| *A61M 5/142* | (2006.01) | |
| *A61M 60/178* | (2021.01) | |
| *A61M 60/216* | (2021.01) | |
| *A61M 60/515* | (2021.01) | |
| *A61M 60/592* | (2021.01) | |
| *G16H 10/60* | (2018.01) | |
| *A61B 5/1455* | (2006.01) | |
| *A61N 1/36* | (2006.01) | |
| *A61B 5/318* | (2021.01) | |
| *G16H 10/20* | (2018.01) | |
| *A61B 5/021* | (2006.01) | |

(52) U.S. Cl.
CPC .......... *A61M 5/142* (2013.01); *A61M 60/178* (2021.01); *A61M 60/216* (2021.01); *A61M 60/515* (2021.01); *A61M 60/592* (2021.01); *G16H 10/60* (2018.01); *A61B 5/0031* (2013.01); *A61B 5/021* (2013.01); *A61B 5/14551* (2013.01); *A61B 5/318* (2021.01); *A61B 5/7465* (2013.01); *A61M 2205/3507* (2013.01); *A61N 1/3605* (2013.01); *G16H 10/20* (2018.01)

(56) References Cited

U.S. PATENT DOCUMENTS

| | | |
|---|---|---|
| 3,888,708 A | 6/1975 | Wise et al. |
| 3,943,915 A | 3/1976 | Severson |
| 4,023,562 A | 5/1977 | Hynecek et al. |
| 4,026,276 A | 5/1977 | Chubbuck |
| 4,037,324 A | 7/1977 | Andreasen |
| 4,067,235 A | 1/1978 | Markland et al. |
| 4,127,110 A | 11/1978 | Bullara |
| 4,206,762 A | 6/1980 | Cosman |
| 4,385,636 A | 5/1983 | Cosman |
| 4,407,296 A | 10/1983 | Anderson |
| 4,485,813 A | 12/1984 | Anderson et al. |
| 4,511,858 A | 4/1985 | Charavit et al. |
| 4,531,526 A | 7/1985 | Genest |
| 4,543,955 A | 10/1985 | Schroeppel |
| 4,567,459 A | 1/1986 | Folger et al. |
| 4,644,420 A | 2/1987 | Buchan |
| 4,651,089 A | 3/1987 | Haigh |
| 4,815,472 A | 3/1989 | Wise et al. |
| 4,881,410 A | 11/1989 | Wise et al. |
| 4,953,387 A | 9/1990 | Johnson et al. |
| 4,966,034 A | 10/1990 | Bock et al. |
| 5,005,577 A | 4/1991 | Frenkel |
| 5,006,819 A | 4/1991 | Buchan et al. |
| 5,013,396 A | 5/1991 | Wise et al. |
| 5,046,497 A | 9/1991 | Millar |
| 5,055,838 A | 10/1991 | Wise et al. |
| 5,058,581 A | 10/1991 | Silvian |
| 5,059,543 A | 10/1991 | Wise et al. |
| 5,108,420 A | 4/1992 | Marks |
| 5,113,868 A | 5/1992 | Wise et al. |
| 5,227,798 A | 7/1993 | Hildebrand |
| 5,257,630 A | 11/1993 | Broitman et al. |
| 5,262,127 A | 11/1993 | Wise et al. |
| 5,282,827 A | 2/1994 | Kensey et al. |
| 5,296,255 A | 3/1994 | Gland et al. |
| 5,334,952 A | 8/1994 | Maddy et al. |
| 5,343,064 A | 8/1994 | Spangler et al. |
| 5,368,040 A | 11/1994 | Carney |
| 5,377,524 A | 1/1995 | Wise et al. |
| 5,417,235 A | 5/1995 | Wise et al. |
| 5,454,270 A | 10/1995 | Brown et al. |
| 5,510,276 A | 4/1996 | Diem et al. |
| 5,564,434 A | 10/1996 | Halperin et al. |
| 5,581,248 A | 12/1996 | Spillman, Jr. et al. |
| 5,690,674 A | 11/1997 | Diaz |
| 5,720,770 A * | 2/1998 | Nappholz .............. H04L 67/18 607/30 |
| 5,840,148 A | 11/1998 | Campbell et al. |
| 5,872,520 A | 2/1999 | Seifert et al. |
| 5,873,835 A | 2/1999 | Hastings |
| 5,920,233 A | 7/1999 | Denny |
| 5,938,602 A | 8/1999 | Lloyd |
| 5,992,769 A | 11/1999 | Wise et al. |
| 6,015,386 A | 1/2000 | Kensey et al. |
| 6,024,704 A | 2/2000 | Meador |
| 6,025,725 A | 2/2000 | Gershenfeld et al. |
| 6,109,113 A | 8/2000 | Chavan et al. |
| 6,111,520 A | 8/2000 | Allen |
| 6,126,675 A | 10/2000 | Shchervinsky et al. |
| 6,140,144 A | 10/2000 | Najafi et al. |
| 6,174,322 B1 | 1/2001 | Schneidt |
| 6,190,400 B1 | 2/2001 | Van De Moer et al. |
| 6,206,835 B1 | 3/2001 | Spillman, Jr. et al. |
| 6,232,150 B1 | 5/2001 | Lin et al. |
| 6,278,379 B1 | 8/2001 | Allen et al. |
| 6,287,256 B1 | 9/2001 | Park et al. |
| 6,309,350 B1 | 10/2001 | VanTassel et al. |
| 6,331,163 B1 | 11/2001 | Kaplan |
| 6,338,284 B1 | 1/2002 | Najafi et al. |
| 6,359,444 B1 | 3/2002 | Grimes |
| 6,366,804 B1 | 4/2002 | Mejia |
| 6,438,408 B1 | 8/2002 | Mulligan et al. |
| 6,447,449 B1 | 9/2002 | Fleischman et al. |
| 6,454,720 B1 | 9/2002 | Clerc et al. |
| 6,459,253 B1 | 10/2002 | Krusell |
| 6,471,656 B1 | 10/2002 | Shalman et al. |
| 6,477,901 B1 | 11/2002 | Tadigadapa et al. |
| 6,499,354 B1 | 12/2002 | Najafi et al. |
| 6,570,457 B2 | 5/2003 | Fischer |
| 6,592,608 B2 | 7/2003 | Fisher et al. |
| 6,636,769 B2 | 10/2003 | Govari et al. |
| 6,645,143 B2 | 11/2003 | VanTassel et al. |
| 6,647,778 B2 | 11/2003 | Sparks |
| 6,658,300 B2 | 12/2003 | Govari et al. |
| 6,666,826 B2 | 12/2003 | Salo et al. |
| 6,667,725 B1 | 12/2003 | Simons et al. |
| 6,680,654 B2 | 1/2004 | Fischer et al. |
| 6,682,490 B2 | 1/2004 | Roy et al. |
| 6,699,186 B1 | 3/2004 | Wolinsky et al. |
| 6,713,828 B1 | 3/2004 | Chavan et al. |
| 6,749,622 B2 | 6/2004 | McGuckin, Jr. et al. |
| 6,764,446 B2 | 7/2004 | Wolinsky et al. |
| 6,779,406 B1 | 8/2004 | Kuzina et al. |
| 6,783,499 B2 | 8/2004 | Schwartz |
| 6,805,667 B2 | 10/2004 | Christopherson et al. |
| 6,817,983 B1 | 11/2004 | Millar |
| 6,824,521 B2 | 11/2004 | Rich et al. |
| 6,838,640 B2 | 1/2005 | Wise et al. |
| 6,844,213 B2 | 1/2005 | Sparks |
| 6,855,115 B2 | 2/2005 | Fonseca et al. |
| 6,890,300 B2 | 5/2005 | Lloyd et al. |
| 6,893,885 B2 | 5/2005 | Lemmerhirt et al. |
| 6,916,310 B2 | 7/2005 | Sommerich |
| 6,923,625 B2 | 8/2005 | Sparks |
| 6,926,670 B2 | 8/2005 | Rich et al. |
| 6,932,114 B2 | 8/2005 | Sparks |
| 6,935,010 B2 | 8/2005 | Tadigadpa et al. |
| 6,939,299 B1 | 9/2005 | Petersen et al. |
| 6,945,939 B2 | 9/2005 | Turcott |
| 6,959,608 B2 | 11/2005 | Bly et al. |
| 6,968,743 B2 | 11/2005 | Rich et al. |
| 6,970,742 B2 | 11/2005 | Mann et al. |
| 6,981,958 B1 | 1/2006 | Gharib et al. |
| 7,001,398 B2 | 2/2006 | Carley et al. |
| 7,004,015 B2 | 2/2006 | Chang-Chien et al. |
| 7,013,734 B2 | 3/2006 | Zdeblick et al. |
| 7,018,337 B2 | 3/2006 | Hood |
| 7,025,727 B2 | 4/2006 | Brockway et al. |
| 7,028,550 B2 | 4/2006 | Zdeblick et al. |
| 7,046,964 B1 | 5/2006 | Sullivan et al. |
| 7,048,756 B2 | 5/2006 | Eggers et al. |
| 7,059,176 B2 | 6/2006 | Sparks |
| 7,059,195 B1 | 6/2006 | Liu et al. |
| 7,066,031 B2 | 6/2006 | Zdeblick et al. |
| 7,073,387 B2 | 7/2006 | Zdeblick et al. |
| 7,081,125 B2 | 7/2006 | Edwards et al. |

(56) References Cited

U.S. PATENT DOCUMENTS

| | | |
|---|---|---|
| 7,137,953 B2 | 11/2006 | Eigler et al. |
| 7,146,861 B1 | 12/2006 | Cook et al. |
| 7,147,604 B1 | 12/2006 | Allen et al. |
| 7,149,587 B2 | 12/2006 | Wardle et al. |
| 7,162,926 B1 | 1/2007 | Guziak et al. |
| 7,174,212 B1 | 2/2007 | Klehn et al. |
| 7,190,937 B1 | 3/2007 | Sullivan et al. |
| 7,191,013 B1 | 3/2007 | Miranda et al. |
| 7,192,001 B2 | 3/2007 | Wise et al. |
| 7,198,603 B2 | 4/2007 | Penner et al. |
| 7,211,048 B1 | 5/2007 | Najafi et al. |
| 7,228,735 B2 | 6/2007 | Sparks et al. |
| 7,245,117 B1 | 7/2007 | Joy et al. |
| 7,273,457 B2 | 9/2007 | Penner |
| 7,274,965 B1 | 9/2007 | Karicheria et al. |
| 7,284,442 B2 | 10/2007 | Fleischman et al. |
| 7,290,454 B2 | 11/2007 | Liu |
| 7,321,337 B2 | 1/2008 | Ikeda et al. |
| 7,353,711 B2 | 4/2008 | O'Dowd et al. |
| 7,401,521 B2 | 7/2008 | Bellini et al. |
| 7,425,200 B2 | 9/2008 | Brockway et al. |
| 7,432,723 B2 | 10/2008 | Ellis et al. |
| 7,466,120 B2 | 12/2008 | Miller et al. |
| 7,483,805 B2 | 1/2009 | Sparks et al. |
| 7,492,144 B2 | 2/2009 | Powers et al. |
| 7,498,799 B2 | 3/2009 | Allen et al. |
| 7,550,978 B2 | 6/2009 | Joy et al. |
| 7,566,308 B2 | 7/2009 | Stahmann |
| 7,574,792 B2 | 8/2009 | O'Brien et al. |
| 7,621,036 B2 | 11/2009 | Cros |
| 7,641,619 B2 | 1/2010 | Penner |
| 7,645,233 B2 | 1/2010 | Tulkki et al. |
| 7,647,831 B2 | 1/2010 | Corcoran et al. |
| 7,662,653 B2 | 2/2010 | O'Brien |
| 7,679,355 B2 | 3/2010 | Allen et al. |
| 7,686,762 B1 | 3/2010 | Najafi et al. |
| 7,686,768 B2 | 3/2010 | Bodecker et al. |
| 7,763,487 B2 | 7/2010 | Villa et al. |
| 7,801,613 B2 | 9/2010 | Li et al. |
| 7,812,416 B2 | 10/2010 | Courcimault |
| 7,839,153 B2 | 11/2010 | Joy et al. |
| 7,899,550 B1 | 3/2011 | Doan et al. |
| 7,932,732 B2 | 4/2011 | Ellis et al. |
| 7,936,174 B2 | 5/2011 | Ellis et al. |
| 7,973,540 B2 | 7/2011 | Kroh et al. |
| 8,014,865 B2 | 9/2011 | Najafi et al. |
| 8,021,307 B2 | 9/2011 | White |
| 8,025,625 B2 | 9/2011 | Allen |
| 8,093,991 B2 | 1/2012 | Stevenson et al. |
| 8,103,361 B2 | 1/2012 | Moser |
| 8,104,358 B1 | 1/2012 | Jia et al. |
| 8,111,150 B2 | 2/2012 | Miller et al. |
| 8,118,748 B2 | 2/2012 | Schugt et al. |
| 8,118,749 B2 | 2/2012 | White |
| 8,132,465 B1 | 3/2012 | Doelle et al. |
| 8,154,389 B2 | 4/2012 | Rowland et al. |
| 8,159,348 B2 | 4/2012 | Ellis |
| 8,237,451 B2 | 8/2012 | Joy et al. |
| 8,267,863 B2 | 9/2012 | Najafi et al. |
| 8,271,093 B2 | 9/2012 | Von Arx |
| 8,353,841 B2 | 1/2013 | White |
| 8,355,777 B2 | 1/2013 | White |
| 8,360,984 B2 | 1/2013 | Yadav et al. |
| 8,373,559 B2 | 2/2013 | McCain |
| 8,424,388 B2 | 4/2013 | Mattes et al. |
| 8,432,265 B2 | 4/2013 | Rowland et al. |
| 8,493,187 B2 | 7/2013 | Rowland et al. |
| 8,506,495 B2 | 8/2013 | Mi et al. |
| 8,512,252 B2 | 8/2013 | Ludomirsky et al. |
| 8,565,866 B2 | 10/2013 | Lomqvist et al. |
| 8,570,186 B2 | 10/2013 | Nagy et al. |
| 8,665,086 B2 | 3/2014 | Miller et al. |
| 8,669,770 B2 | 3/2014 | Cros |
| 8,676,349 B2 | 3/2014 | Stalker |
| 8,700,924 B2 | 4/2014 | Mian et al. |
| 8,852,099 B2 | 10/2014 | Von Arx et al. |
| 8,866,788 B1 | 10/2014 | Birnbaum |
| 8,870,787 B2 | 10/2014 | Yadav et al. |
| 8,901,775 B2 | 12/2014 | Armstrong et al. |
| 9,044,150 B2 | 6/2015 | Brumback |
| 9,078,563 B2 | 7/2015 | Cros |
| 9,265,428 B2 | 2/2016 | O'Brien et al. |
| 9,305,456 B2 | 4/2016 | Rowland et al. |
| 9,489,831 B2 | 11/2016 | Nagy et al. |
| 9,496,924 B2 | 11/2016 | Aber et al. |
| 9,498,130 B2 | 11/2016 | Friedman et al. |
| 9,504,423 B1 | 11/2016 | Bardy et al. |
| 9,712,894 B2 | 7/2017 | Lee et al. |
| 9,723,987 B2 * | 8/2017 | Goetz .................. A61B 5/0031 |
| 9,723,997 B1 | 8/2017 | Lamego |
| 9,839,732 B2 | 12/2017 | Armstrong et al. |
| 9,867,552 B2 | 1/2018 | Rowland et al. |
| 9,996,712 B2 | 6/2018 | Nagy et al. |
| 10,003,862 B2 | 6/2018 | Rowland et al. |
| 10,022,054 B2 | 7/2018 | Najafi et al. |
| 10,105,103 B2 | 10/2018 | Goldshtein et al. |
| 10,143,388 B2 | 12/2018 | Cros et al. |
| 10,205,488 B2 | 2/2019 | Hershko et al. |
| 10,307,067 B1 | 6/2019 | Xu |
| 10,383,575 B2 | 8/2019 | Najafi et al. |
| 10,478,067 B2 | 11/2019 | Najafi et al. |
| 10,687,709 B2 | 6/2020 | Najafi et al. |
| 10,687,716 B2 | 6/2020 | Goldshtein et al. |
| 10,709,341 B2 | 7/2020 | White et al. |
| 10,874,349 B2 | 12/2020 | Goldshtein et al. |
| 10,874,479 B2 | 12/2020 | Forsell |
| 11,154,207 B2 | 10/2021 | Campbell et al. |
| 11,206,988 B2 | 12/2021 | Goldshtein et al. |
| 2002/0111662 A1 | 8/2002 | Iaizzo |
| 2003/0125790 A1 | 7/2003 | Fastovsky |
| 2004/0152957 A1 * | 8/2004 | Stivoric .................. A61B 5/11 600/300 |
| 2005/0121734 A1 | 6/2005 | Degertekin |
| 2005/0197674 A1 * | 9/2005 | McCabe ................ A61N 1/365 607/9 |
| 2006/0064036 A1 | 3/2006 | Osborne |
| 2006/0094970 A1 * | 5/2006 | Drew .................... A61B 5/318 600/509 |
| 2006/0287602 A1 | 12/2006 | O'Brien et al. |
| 2007/0163355 A1 | 7/2007 | Nassar et al. |
| 2007/0208390 A1 | 9/2007 | Von Arx et al. |
| 2007/0220006 A1 * | 9/2007 | Elletson ................ G16H 10/60 |
| 2007/0255156 A1 * | 11/2007 | Mertz ................ A61N 1/37512 600/527 |
| 2007/0255337 A1 * | 11/2007 | Lu ...................... A61N 1/36007 607/40 |
| 2008/0269573 A1 * | 10/2008 | Najafi .................... A61B 5/076 600/301 |
| 2009/0221885 A1 | 9/2009 | Hall et al. |
| 2009/0299672 A1 | 12/2009 | Zhang et al. |
| 2011/0004076 A1 * | 1/2011 | Janna .................... A61B 5/076 600/302 |
| 2011/0022411 A1 * | 1/2011 | Hjelm .................... G16H 10/60 705/2 |
| 2013/0204100 A1 | 8/2013 | Acauista |
| 2016/0324443 A1 | 11/2016 | Rowland et al. |
| 2020/0022601 A1 | 1/2020 | Rogers et al. |
| 2020/0297218 A1 | 9/2020 | White et al. |
| 2021/0068681 A1 | 3/2021 | Campbell et al. |
| 2021/0275733 A1 | 9/2021 | Goldshtein et al. |

FOREIGN PATENT DOCUMENTS

| | | |
|---|---|---|
| CN | 1826686 | 8/2006 |
| CN | 101116322 | 1/2008 |
| CN | 101128957 | 2/2008 |
| CN | 101278439 | 10/2008 |
| CN | 101427923 | 5/2009 |
| HK | 1147906 | 8/2011 |
| JP | 2000005136 | 1/2000 |
| JP | 2000-517073 | 12/2000 |
| JP | 2002515278 | 5/2002 |
| JP | 2003144417 | 5/2003 |

(56) References Cited

FOREIGN PATENT DOCUMENTS

| | | |
|---|---|---|
| JP | 2005284511 | 10/2005 |
| JP | 2006-512112 | 4/2006 |
| JP | 2006309582 | 11/2006 |
| JP | 2007-210547 | 8/2007 |
| JP | 2007256287 | 10/2007 |
| JP | 2008022935 | 2/2008 |
| JP | 2008-532590 | 8/2008 |
| JP | 2010538254 | 12/2010 |
| KR | 20130118479 | 10/2013 |
| WO | 2004/045407 | 6/2004 |
| WO | 2005/018507 | 3/2005 |
| WO | 2005/107583 | 11/2005 |
| WO | 2005115533 A2 | 12/2005 |
| WO | 2006/070278 | 7/2006 |
| WO | 2006/096582 | 9/2006 |
| WO | 2006/130488 | 12/2006 |
| WO | 2007/030489 | 3/2007 |
| WO | 2007131066 A2 | 11/2007 |
| WO | 2008/091409 | 7/2008 |
| WO | 2008/098255 | 8/2008 |
| WO | 2008/115456 | 9/2008 |
| WO | 2008/137703 | 11/2008 |
| WO | 2009146089 | 12/2009 |
| WO | 2010/117356 | 10/2010 |
| WO | 2010/117597 | 10/2010 |
| WO | 20120149008 | 1/2012 |
| WO | 2012015955 | 2/2012 |
| WO | 2013033506 | 3/2013 |
| WO | 2014170771 A1 | 10/2014 |
| WO | 2017115112 | 7/2017 |

OTHER PUBLICATIONS

Patent Cooperation Treaty (PCT), International Search Report and Written Opinion for Application PCT/US12/44998, dated Sep. 25, 2012, 9 pgs., International Searching Authority, US.
Extended European Search Report for Application 12804636.4 PCT/US2012044998, dated Jan. 20, 2015, 6pgs., Eurpoean Patent Office, Germany.
Patent Cooperation Treaty (PCT), International Search Report and Written Opinion for Application PCT/US/14/30661, dated Sep. 17, 2015, 8 pp., Interational Searching Authority, US.
Extended European Search Report for Application 14806873.7 PCT/US2014030661, dated May 20, 2016, 7 pp., European Patent Office, Germany.
Extended European Search Report for application EP13850155.6, PCT/US2013/059769, dated Apr. 19, 2016, European Patent Office, Germany.
Patent Cooperation Treaty (PCT), International Search Report and Written Opinion for application PCT/US2013/059769, dated Dec. 13, 2013, International Searching Authority, US.
Patent Cooperation Treaty (PCT), International Search Report and Written Opinion for application PCT/US2011/045583, dated Nov. 23, 2011, International Searching Authority, NL.
AU Patent Examination Report No. 1 for application AU2012275126, dated Apr. 9, 2016, Australian Government IP Australia, Australia.
Patent Cooperation Treaty (PCT), International Search Report and Written Opinion for application PCT/US2011/045581, dated Oct. 18, 2011, International Searching Authority, US.
Patent Cooperation Treaty (PCT), International Search Report and Written Opinion for application PCT/US2008/69229, dated Oct. 1, 2008, International Searching Authority, US.
Abrams, Synopsis of Cardiac Physical Diagnosis, 1989, Lea & Febiger, pp. 25-29.
Ganong, Review of Medical Physiology, 2003, 21st edition, The McGraw-Hill, Inc., Chapter 29, pp. 569-573.
Allen et al., Moss and Adams' heart Disease in Infants, Children, and Adolescents, including the Fetus and Young Adult, 2001, Lippincott Williams & Wilkins, 6th edition, vol. 1, pp. 288-292.
AU Patent Examination Report No. 1 for application AU2010235020, dated Aug. 18, 2014, Australian Government IP Australia, Australia.
CA Examination Report for application CA2757952, PCT/US2010/027951, dated Oct. 28, 2015, Canadian Intellectual Property Office, Canada.
Extended European Search Report for application EP10762085.8, PCT/2010027951, dated Jan. 4, 2013, European Patent Office, Germany.
PK Examination Report for application PK189/2011, emailed Jun. 6, 2013, Pakistan Patent Office, Pakistan.
Haynes, H.E. & Witchey, A.L., Medical Electronics; The Pill That "Talks" DEP, 1960, pp. 52-54, Cambden, New Jersey.
Collins, Carter, Miniature Passive Pressure Transensor for Implanting in the Eye, Transactions on Bio-Medical Engineering, vol. BME-14, No. 2, pp. 74-83, Apr. 1967.
Nagumo, J., Uchiyama, A., Kimoto, S., Watanuki, T., Hori, M., Suma, K., Ouchi, A., Kumano, M., and Watanabe, H., Echo Capsule for Medical Use (A Batteryless Endoradiosonde), IRE Transaction on Bio-Medical Electronics, pp. 195-199, 1962.
Patent Cooperation Treaty (PCT), International Search Report and Written Opinion for application PCT/US2010/27951, dated Aug. 25, 2010, International Searching Authority, US.
Patent Cooperation Treaty (PCT), Written Opinion of the International Searching Authority for application PCT/US2008/03475, dated Aug. 4, 2008, International Searching Authority, US.
Patent Cooperation Treaty (PCT), Written Opinion of the International Searching Authority for application PCT/US2009/39730, dated Jun. 30, 2009, International Searching Authority, US.
International Preliminary Report on Patentability, Endotronix, Inc. PCT/US2012/034979, dated Nov. 7, 2013.
International Search Report and the Written Opinion of the International Searching Authority, Endotronix, Inc., PCT/US2012/34979, dated Nov. 2, 2012.
International Preliminary Report on Patentability, Nunez, Anthony, I. et al. PCT/US2008/003475, dated Sep. 24, 2009.
Communication pursuant to Article 94(3) EPC from the European Patent Office; Application No. 10 762 085.8-1660; dated Jan. 26, 2015.
Communication pursuant to Article 94(3) EPC from the European Patent Office; Application No. 10 762 085.8-1660; dated Sep. 17, 2015.
International Search Report and Written Opinion prepared for PCT/US2016/050081 dated Dec. 2, 2016.
European Office Action dated Apr. 6, 2021; European Patent Application No. 18755995.0.
Klein et al., "Risk stratification for implantable cardioverter defibrillator therapy: the role of the wearable cardioverter-defibrillator" European Hear Journal, vol. 34, No. 29, pp. 2230-2242. (May 31, 2013).

* cited by examiner

PHYSIOLOGICAL MONITORING SYSTEM

CROSS REFERENCE TO RELATED APPLICATIONS

This application claims priority to U.S. Provisional Patent Application Ser. No. 62/534,261 filed on Jul. 19, 2017, which is incorporated by reference herein.

TECHNICAL FIELD

This invention relates generally to a physiological monitoring system for measuring, communicating, tracking, and recording various physiologic data from a patient.

BACKGROUND

A conventional healthcare delivery system may include a clinician or care management team such as doctors, nurses, physician assistants, etc. that interacts with an integrated information system such as a computer system running various data management programs. The information system may be populated with patient data in an electronic medical record database. Within this healthcare delivery context, a significant problem exists in that while the patient may be fully monitored while being treated by the care management team, once the patient progresses from in-patient to out-patient, healthcare delivery is often reduced in quality because of lack of adequate monitoring of the patient. Furthermore, the clinician may comprise a number of unrelated healthcare professionals that may not communicate with each other or the hospital. This disconnected nature of the system may result in patients receiving improper care.

Various systems have been created in an attempt to solve these issues. In particular, various computer implemented methods have been adapted to improve communication to bridge the gap between clinicians and monitoring of patient physiologic data. Commonly, bedside physiological monitoring systems are implemented at hospitals to constantly monitor patients during their stay. Many of these methods incorporate computer systems to monitor physiologic data taken from peripheral devices that may be categorized as non-invasive such as blood pressure cuffs, oxygen sensors or weight scales. Some of these devices are even available in the home of the patient. However, these methods and systems are not capable of interacting with peripheral devices that include more invasive monitoring techniques, such as implants.

In the United States, the U.S. Food and Drug Administration (FDA) regulates the commercialization of medical devices and systems. The FDA classifies medical devices based on the risks associated with the device. As such, devices and systems are classified into one of three categories—Class I, Class II, and Class III. Class I devices are deemed to be low risk and are therefore subject to the least regulatory controls. For example, a weight scale is classified as Class I device. Class II devices are higher risk devices than Class I and require greater regulatory controls to provide reasonable assurance of the device's safety and effectiveness. For example, noninvasive blood pressure measurement systems are Class II devices. A noninvasive blood pressure measurement system is identified by the FDA as a device that provides a signal from which systolic, diastolic, mean, or any combination of the three pressures can be derived through the use of transducers placed on the surface of the body. Class III devices are generally the highest risk devices and are therefore subject to the highest level of regulatory control. Class III devices must typically be approved by FDA before they are free to be commercialized. For example, replacement heart valves and implantable pacemaker pulse generators are classified as Class III devices.

Thus, there is a need to provide an improved system for managing and monitoring physiological measurements from both non-invasive peripheral devices as well as invasive types of peripheral devices. Additionally, there is also a need to be able to provide this system at the residence of the patient or a more mobile system for use by patients outside of a hospital or clinic. Further, there is a need to provide a method of care for chronic end stage diseases that incorporates a system of various components to streamline communication and ease of implementation.

BRIEF DESCRIPTION OF THE DRAWINGS

Objects and advantages together with the operation of the invention may be better understood by reference to the following detailed description taken in connection with the following illustrations, wherein.

SUMMARY

Figure 1:
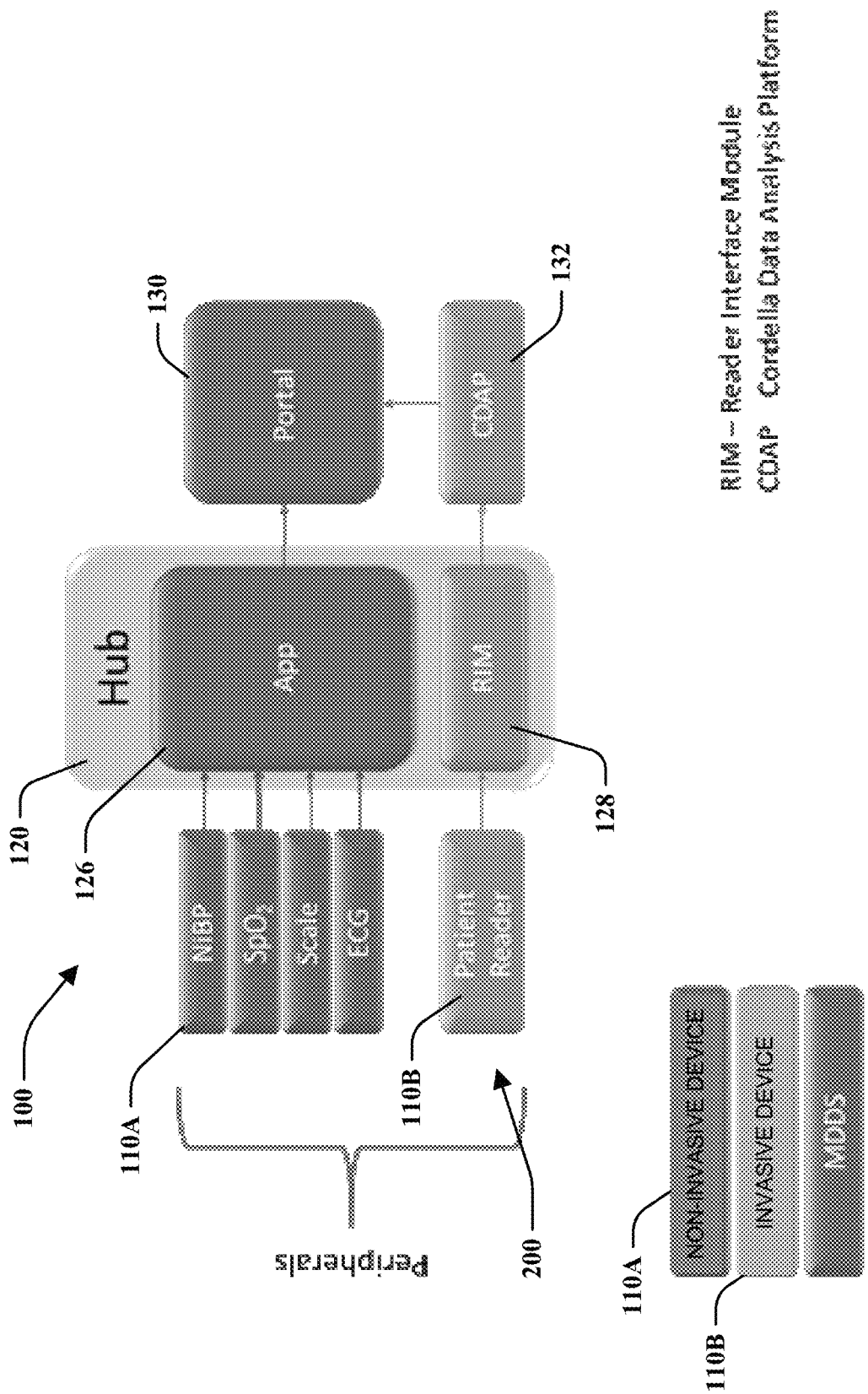
FIG. 1 illustrates a block diagram of an embodiment of a physiological monitoring system in accordance with the instant disclosure.

Disclosed is a physiologic monitoring system comprising a central hub in communication with a management portal. At least one non-invasive peripheral device may measure physiologic data from a patient in communication with said central hub and an invasive peripheral system associated with said patient may be in communication with said central hub. The central hub may be scalable to collect data and communicate with the non-invasive peripheral device and the invasive peripheral system such that data from the non-invasive peripheral device and the invasive peripheral system are selectively communicated to the management portal. The at least one non-invasive peripheral device may include a blood pressure cuff, an oxygen sensor, a weight scale, and an ECG monitor. The invasive peripheral system may include an invasive peripheral device, wherein said invasive peripheral device includes at least one of an implantable sensor an actuator, a dialysis assembly, a drug delivery device, an infusion pump, a neuro-stimulation assembly, an oxygen delivery system, or a ventricular assistance device. A wireless sensor reader and a docking station may be part of the invasive peripheral system wherein the wireless sensor reader may be adapted to measure physiologic data from an implantable sensor placed within a cardiovascular system of said patient. The central hub may include a graphical user interface for displaying a patient application. The central hub may include a reader interface module in communication with the invasive peripheral system. The management portal may be in communication with a data analysis platform that is configured to receive data from the reader interface module, analyze the received data to generate processed data and communicate the processed data to the management portal.

In another embodiment, provided is a method of monitoring physiologic data comprising the step of measuring physiologic data from a patient with at least one non-invasive peripheral device. The step of measuring physiologic data from said patient with a system that includes an invasive peripheral device. The step of communicating said physiologic data to a central hub; and the step of communicating said physiologic data to a management portal to display to a clinical specialist. A plurality of health-related questions may be generated by the central hub to be answered by the patient and communicated to the management hub for display to the clinical specialist. The physiologic data may be aggregated and displayed by the central hub. The physiologic data may be aggregated and displayed at the management portal. The non-invasive peripheral device may include at least one of a blood pressure cuff, an oxygen sensor, a weight scale, and an ECG monitor. The invasive peripheral device may include at least one of an implantable sensor, an actuator, a dialysis assembly, a drug delivery device, an infusion pump, a neuro-stimulation assembly, an oxygen delivery system, or a ventricular assistance device. The implantable sensor and a wireless sensor reader may communicate to measure physiologic data from said implantable sensor placed within a cardiovascular system of said patient. Physiologic data measured from a patient with at least one non invasive peripheral device may be communicated to the management portal to display to said clinical specialist, wherein said clinical specialist analyzes said communicated physiologic data to prescribe an invasive peripheral device for use by said patient. The measured physiologic data may be communicated to a reader interface module of the central hub from the invasive peripheral device. The measured physiologic data from said invasive peripheral device may be communicated to a data analysis platform from the reader interface module wherein said data analysis platform analyzes said measured physiologic data and generates processed data wherein said processed data is communicated to the management portal.

In another embodiment, provided is a physiologic monitoring system comprising a central hub in communication with a management portal, said central hub includes a reader interface module and a graphical user interface for displaying a patient application. At least one non-invasive peripheral device to measure physiologic data from a patient in communication with said central hub. A peripheral system that includes an invasive peripheral device to measure physiologic data from said patient in communication with said central hub, the peripheral system is in communication with said reader interface module. The central hub is scalable to collect and communicate measurements from the non-invasive peripheral device and the invasive peripheral device. The management portal may be in communication with a data analysis platform configured to receive data from said reader interface module and display said data at the management portal. The at least one non-invasive peripheral device includes a blood pressure cuff, an oxygen sensor, a weight scale, and an ECG monitor. The invasive peripheral device includes an implantable sensor. The data analysis platform may be configured to interface with the peripheral system and the invasive peripheral device to calibrate said invasive peripheral device.

In another embodiment, provided is a method of monitoring physiologic data comprising measuring physiologic data from a patient with at least one non invasive peripheral device. Physiologic data is communicated to a central hub, said central hub includes a reader interface module. Physiologic data is communicated to a management portal to display to a specialist clinician. The communicated physiologic data is analyzed to prescribe a system that includes an invasive peripheral device for use by the patient. Physiologic data may be measured from said patient with said system that includes said invasive peripheral device. Physiologic data may be communicated to said reader interface module of said central hub. Physiologic data may be communicated to said management portal to display to a clinician specialist. The physiologic data may be aggregated and displayed at the management portal. The non-invasive peripheral device includes at least one of a blood pressure cuff, an oxygen sensor, a weight scale, and an ECG monitor. The invasive peripheral device includes at least one of an implantable sensor, an actuator, a dialysis assembly, a drug delivery device, an infusion pump, a neuro-stimulation assembly, an oxygen delivery system, or a ventricular assistance device.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the present invention.

The disclosed physiological monitoring system 100 collects, records, and transmits physiologic data from the patient to clinician(s) for assessment, patient communication, and patient-centered heart health management. The physiologic monitoring system includes the ability to monitor blood pressure, heart rate, blood oxygen, weight and responses to heart failure guideline-directed health assessment questions while the patient may be located remotely from the clinician. The monitoring system may be adapted for use with various peripheral devices for physiological measurements such as a blood pressure cuff, a pulse oximetry sensor, and a weight scale while also being adapted for use with a system that incorporates an invasive peripheral device. In one embodiment, an invasive system may be referred to herein as the Cordella™ Pulmonary Artery Sensing System (CorPASS) 200. The CorPASS 200 is a system that is designed to measure pulmonary artery blood pressure from an implant sensor placed within the cardiovascular system of a patient. In other embodiments, an invasive system may include an invasive peripheral device such as an implantable sensor, an actuator, a dialysis assembly, a drug delivery device, an infusion pump, a neurostimulation assembly, an oxygen delivery system, or a ventricular assistance device.

It is a focus of the instant disclosure to provide monitoring of end stage diseases and allow a clinical specialists in the related field of such end stage disease to oversee that monitoring. End stage diseases may include diseases that have no known cure such as heart failure and kidney failure as well as certain types of cancers. The system and method of the instant disclosure focuses to provide permanent chronic care for end stage diseases wherein such care is provided by clinical specialists in the field such as a cardiologist, nephrologist, or even an oncologist and related staff members with authorization. Further, it is also a focus of the instant disclosure to provide such care in a way that optimizes the interaction between the clinical specialists (or staff member overseen by the clinical specialist in the field) by specifically tailoring a management portal to the clinical workflow of the clinical specialists.

Figure 2:
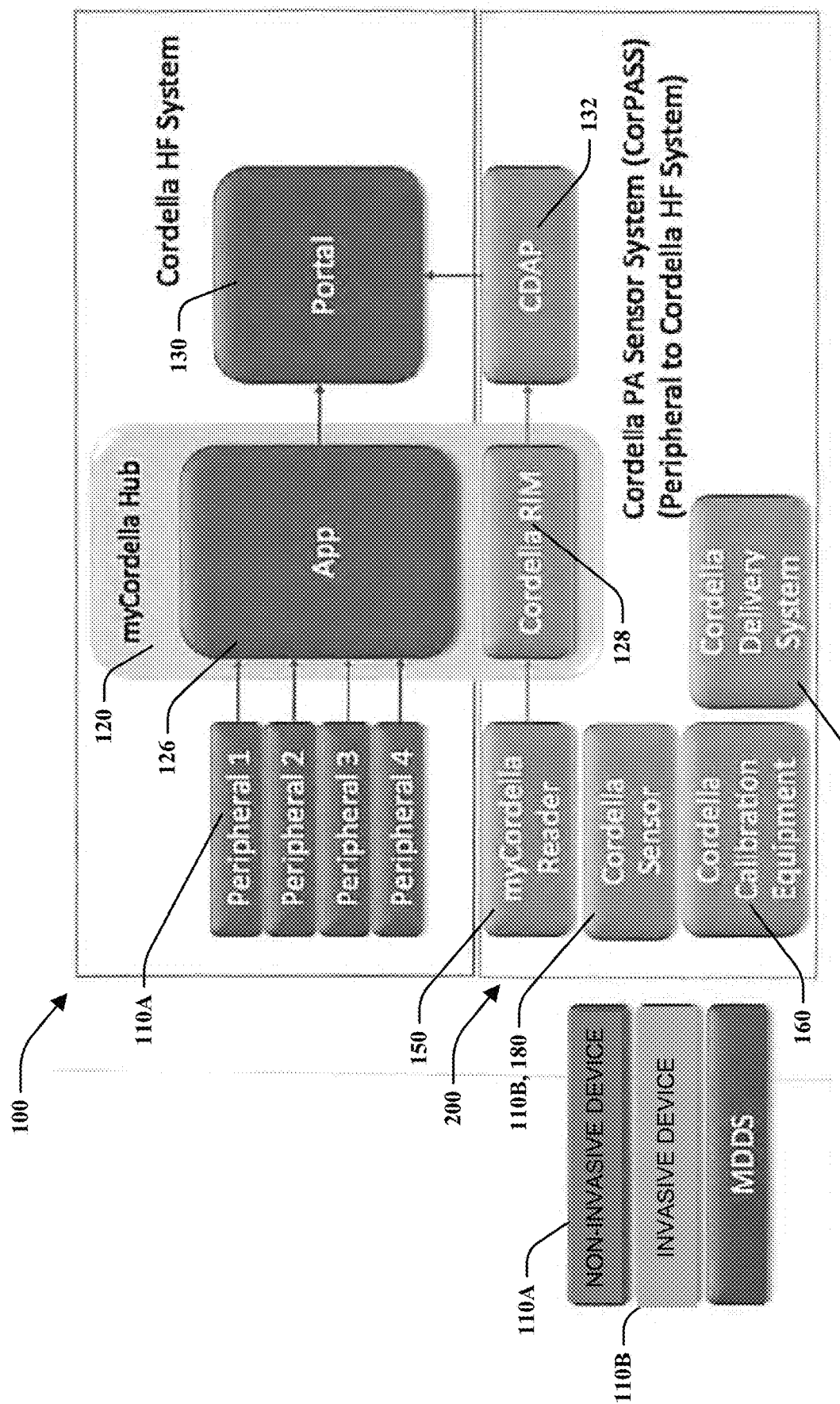
FIG. 2 illustrates a block diagram of another embodiment of a physiological monitoring system in accordance with the instant disclosure.
Figure 4:
FIG. 4 illustrates an embodiment of a docking station for the reader device that may be a peripheral device to the physiological monitoring system of the instant disclosure.
Figure 3:
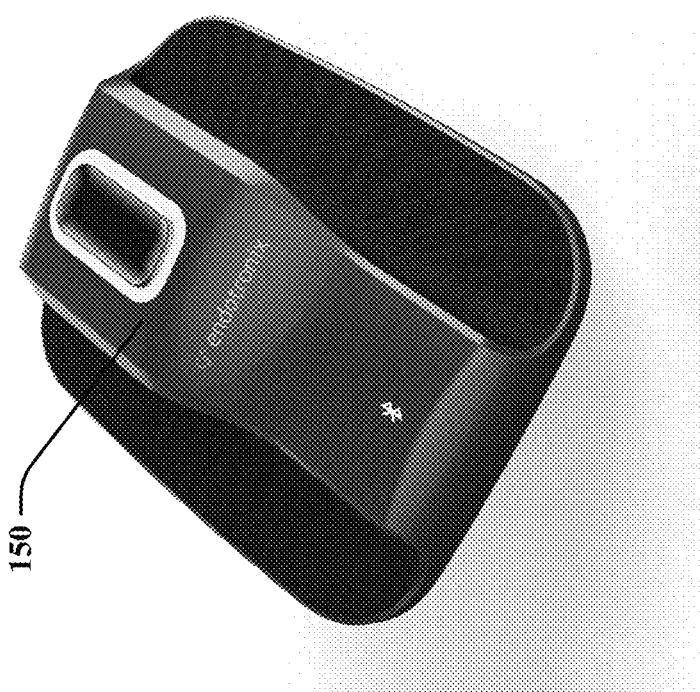
FIG. 3 illustrates an embodiment of a reader device that may be a peripheral device to the physiological monitoring system of the instant disclosure.
Figure 5:
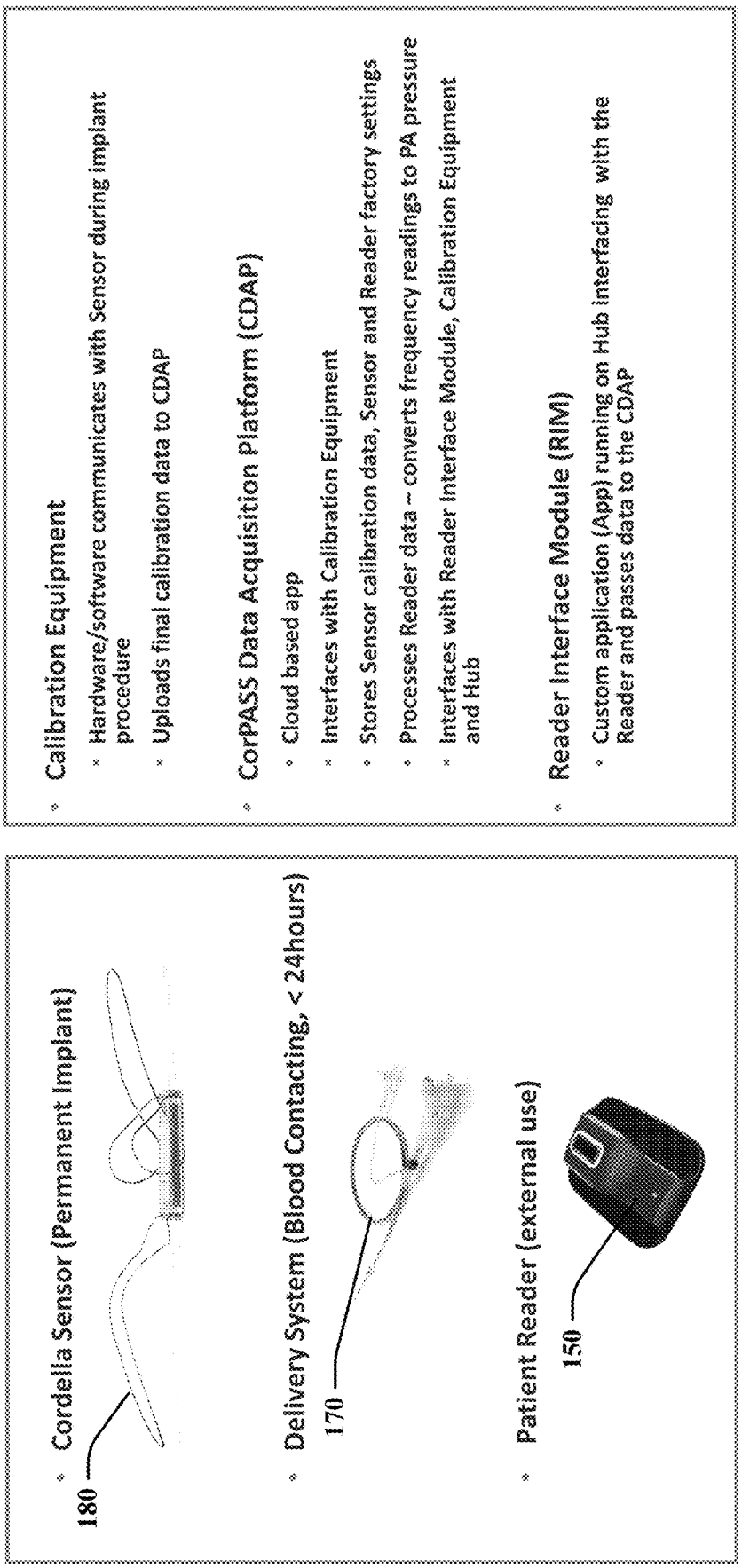
FIG. 5 illustrates an implant that may be implanted in a cardiovascular system of a patient which may be a peripheral device to the physiological monitoring system of the instant disclosure.

As illustrated by FIGS. 1 and 2, the monitoring system 100 includes a plurality of peripheral devices 110A, 110B, a central hub 120, and a management portal 130. The peripheral devices may include non-invasive devices 110A and invasive devices 110B as will be discussed more fully herein. The monitoring system 100 allows a user to collect data from a patient via the peripherals 110A, 110B and then transmit the data from the central hub 120 to the management portal 130 through a communication network. The system 100 may include a central database may record the data and allow for retrospective review of patient physiological functions.

It is noted that user equipment devices including the central hub 120, management portal 130 and the peripheral devices 110A, 110B can communicate with each other and with other elements via a network, for instance, a wireless network, or a wireline network. A "network" can include broadband wide-area networks such as cellular networks, local-area networks, wireless local-area networks (e.g., Wi-Fi), and personal area networks, such as near-field communication networks including BLUETOOTH®. Communication across a network may include packet-based communications, radio and frequency/amplitude modulations networks, and the like. In those embodiments in which it is hardwired, any appropriate kind or type of networking cables may be utilized. For example, USB cables, dedicated wires, coaxial cables, optical fiber cables, twisted pair cables, Ethernet, HDMI and the like.

The peripheral devices 110A, 110B may be adapted to collect various vital signals from a patient and communicate these signals to the central hub 120. The peripheral devices may include non-invasive peripheral devices 110A. These non-invasive peripheral devices 110A may include a non-invasive blood pressure monitor (NiBP), a blood oxygen saturation level monitor (SpO2), a weight scale (Scale), an electrocardiogram monitor (ECG) or other patient device for measuring vital signs such as, for example, glucose levels. Additionally, an invasive peripheral device 110B may also be adapted to communicate with the central hub 120 in a particular manner. An example of an invasive peripheral device 110B includes an implantable sensor surgically positioned within the body of a patient and its associated components to take readings from the implantable sensor, however this application is not limited to just one type of invasive peripheral system and device and the system may be scalable to include various types of invasive devices.

The CorPASS system 200 is an example of an invasive peripheral system that incorporates an invasive peripheral device 110B. As illustrated by FIGS. 3-6, the CorPASS system 200 may include an implant sensor 180, a delivery system 170, a reader 150, and a docking station (calibration equipment) 160. The wireless sensor reader 150 includes various features and may take readings of the implant sensor 180 within the cardiovascular system of a patient.

Current designs for wireless sensor readers that communicate with invasive sensors, are disclosed in U.S. Provisional Patent Application No. 62/463,203 filed on Feb. 24, 2017, U.S. Pat. No. 8,154,389 filed on Apr. 7, 2008, U.S. Pat. No. 8,432,265 filed on Mar. 19, 2012, U.S. Pat. No. 8,493,187 filed on Mar. 19, 2010, and U.S. Pat. No. 8,570,186 filed on Apr. 25, 2012, U.S. patent application Ser. No. 14/842,973 filed on Sep. 2, 2015, and U.S. patent application Ser. No. 15/213,712 filed on Jul. 19, 2016, each of which are incorporated by reference in their entireties herein. These patents disclose systems configured to communicate wirelessly with an implant and obtain a reading.

The implant sensor 180 may take pulmonary artery pressure measurements and communicate them to the wireless sensor reader 150. Examples of an implant sensor 180 are disclosed in U.S. patent application Ser. No. 15/213,712 filed Jul. 19, 2016 and its related family of patents, each of which are incorporated by reference in their entireties. Delivery systems 170 for implanting the sensor into a patient are disclosed in PCT Patent Application No. PCT/US2011/45583 titled PRESSURE SENSOR, CENTERING ANCHOR, DELIVERY SYSTEM AND METHOD, which is also incorporated by reference in its entirety herein. A docking station 160 may receive and communicate with the reader 150 as well as charge and calibrate the reader 150. The docking station 160 may be an example of calibration equipment comprising hardware and software that communicates with the sensor during an implant procedure. An example of a docking station 160 is disclosed in U.S. patent application Ser. No. 14/842,973, which is incorporated by reference in its entirety herein. The CorPASS system 200 may be useful in assisting diagnosis and treatment of many diseases. For the purposes of clarity, the peripheral device 110B of the CorPASS system may be either the reader 150 or the docking station 160 as either device may be configured to communicate with the central hub 120.

End stage diseases may have various categories or stages based on the severity of the disease. For example, the New York Heart Association (NYHA) classifies heart failure between class I through class IV depending upon severity. Further, kidney failure is also classified to be between stage 1 and stage 5 depending upon severity. Thus, it may be particularly relevant for early class or early stage patients that utilize the monitoring system 100 with only having non-invasive peripheral devices 110A during such early class or early stages of end stage diseases to assist the clinical specialists to identify if the patient is a candidate for receiving care that utilizes a system that incorporates an invasive peripheral system and device 110B for monitoring or otherwise actuating or dispensing medical care. In such a scenario, it is contemplated that the monitoring system 100 may provide physiological data from non-invasive peripheral devices 110A such that the clinician may analyze the data to diagnose the existence that late stage, late class, or chronic end stage disease may be occurring in a patient wherein invasive steps are necessary for providing appropriate further care. Notification of such a progression from early stage/early class to late stage/late class may occur over time while a patient has been utilizing the monitoring system 100 without use of an invasive peripheral device 110B wherein as the patient has been prescribed use of such an invasive peripheral device 110B, the monitoring system 100 provides for seamless integration with both the non-invasive and invasive peripheral devices 110A, 110B such that an improvement in appropriate care may be provided. This seamless integration of the monitoring system 100 allows for monitoring of physiologic data as well as efficiently accepting, processing, and transferring data from all devices 110A, 110B.

Figure 7:
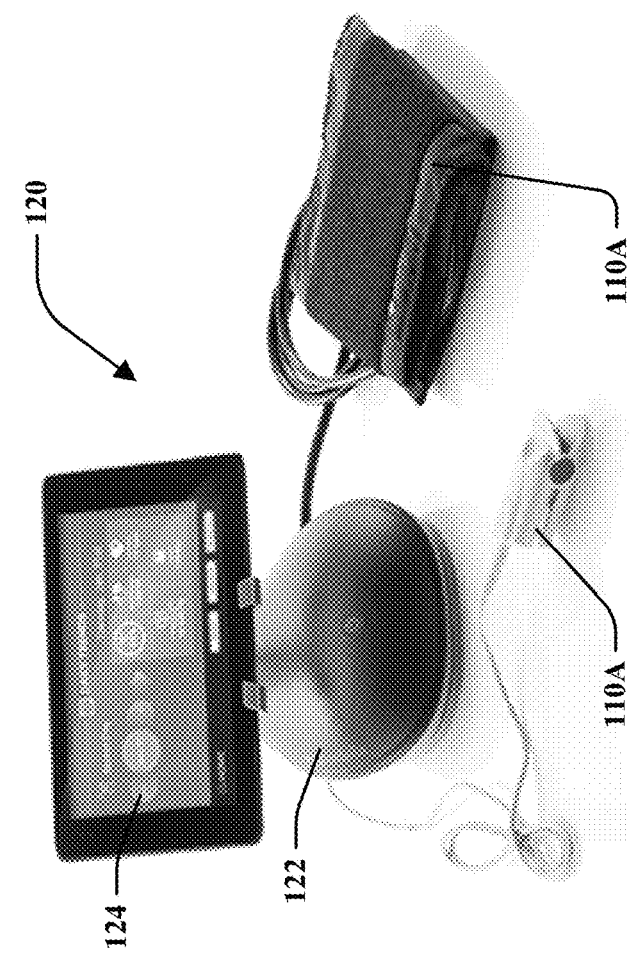
FIG. 7 illustrates a portal of the physiological monitoring system.
Figure 6:
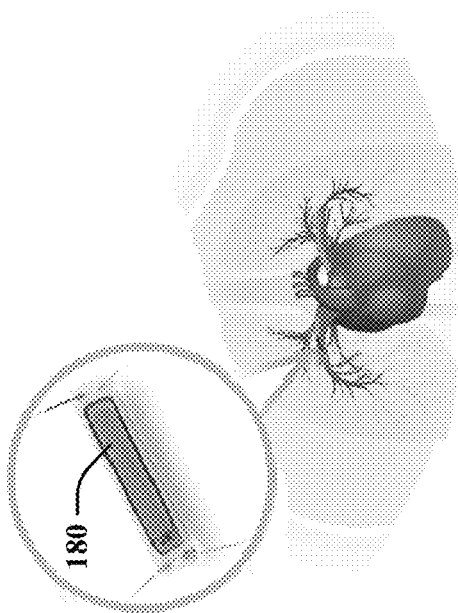
FIG. 6 illustrates a hub, a graphical use interface, a cuff, and an oxygen sensor of the physiological monitoring system.

FIG. 7 illustrates an embodiment of the central hub 120 and various non-invasive peripheral devices 110A including a non-invasive blood pressure monitor (NiBP) and a blood oxygen saturation level monitor (SpO2). The central hub 120 may include a base 122 and a graphical user interface 124. The base 122 may include various ports for selective attachment to the peripherals and the graphical user interface 124. The base 122 may include at least one input or switch to toggle power to or various modes of the system 100. The graphical user interface 124 may be on a patient facing monitor that displays a program identified herein as a patient application 126 (FIGS. 1 and 2). Alternatively, the central hub 120 may be a tablet, cell phone, laptop, or other computing device. The patient application 126 may be stored in a computer readable medium or database or be a web based application accessible through the central hub 120. The patient application 126 may be an interactive program that prompts a patient to provide answers to various questions that may be material to a clinical diagnosis. The patient application 126 may be a standalone program that is adapted to remind the patient to obtain physiologic measurements and respond to health-related questions. Further, the patient application 126 may include instructions to the patient to identify how to properly use the peripheral devices and how to collect measurements representative of biometric or physiologic data. Once measurements have been taken, the patient application 126 may aggregate the collected data and may analyze that data to determine a status of the patient's health. Alternatively, the patient application 126 may aggregate the collected data and send it to the clinical portal 130 or another database where analysis of the data may take place to determine a status of the patient's health, such as a database designed for artificial intelligence or machine learning. Alternatively, the patient application 126 may aggregate the collected data and send it to the clinical portal 130 or another database where analysis of the data may take place by a clinician or other medical care provider to determine a status of the patient's health. The patient application 126 may receive various types of data from an external database to display to the patient. The patient application 126 may generate or display a summary or snapshot of the patient's health status and related data or messages that may be displayed on the graphical user interface 124. The collected physiologic data and patient's health status information may be communicated to the management portal 130. The central hub 120 may be particularly located at a patient's residence or be remotely located from a clinician's office or hospital.

The central hub 120 may also include a reader interface module (RIM) 128 that is a subsystem to the patient application 126. The RIM 128 may be a program stored on a computer readable medium that is configured to communicate with the CorPASS system 200 or with other invasive peripheral systems and in particular the invasive peripheral device 110B. The RIM 128 may function separately from the patient application 126 but may communicate information to the patient application 126 to allow information to be displayed on the graphical user interface 124. The interaction between the patient application 126 and the RIM 128 includes separate functionality as the patient application 126 is designed to communicate with non-invasive peripheral devices 110A while the RIM 128 is designed to communicate with invasive peripheral devices 110B. The separate functionality may exist within the central hub 120 such that the hub 120 may be scalable to function with only non-invasive peripheral devices 110A, with only the invasive peripheral devices 110B, or with both non-invasive and invasive devices 110A, 110B. The RIM 128 may be a custom application running on the hub 120 that interfaces with the reader 150 and/or docking station 160 and passes collected physiologic data to a data analysis platform 132.

Figure 8:
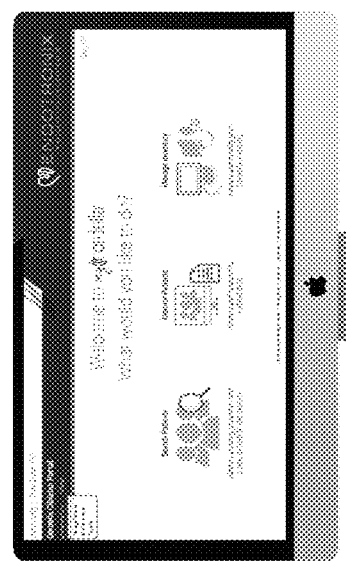
FIG. 8 illustrates a diagram including peripheral devices of the physiological monitoring system.

As illustrated by FIG. 8, the management portal 130 may be a clinic facing application that is intended to be accessible by a clinician. The management portal 130, as shown by FIG. 8, may be an interactive program that is stored in a computer readable medium or database. Alternatively, the portal 130 may be a web-based application that is displayed on a clinic facing display such as a computer, tablet, smartphone or other device. The management portal 130 may aggregate and display the collected physiologic data or patient's health status information and other related data or messages from the hub 120. This information may include physiologic data measured from the peripheral devices 110A, 110B as well as patient responses to various questions including health related questions that have been transported by the central hub 120.

The management portal 130 is specifically tailored to be optimized for a clinical workflow of clinical specialists and associated medical care providers. The particular clinical specialists contemplated by this disclosure includes cardiologists, nephrologists, orthopedist, gastroenterologist, hepatologist, neurologist, psychiatrist, critical care specialists, endocrinologist, oncologist, and ophthalmologists. The clinical workflow of clinical specialists include clinician facing dashboards set up to minimize time spent reviewing the monitored physiologic data and messages and also to track the clinician's time and billing data for interfacing with billing related programs and systems. For example, in a typical cardiologist clinic, a single nurse may manage a high number of patients wherein that nurse or clinician is allotted a minimal amount of time, such as only 15 minutes per patient per week. The management portal 130 is optimized to minimize interruption of workflow tendencies, is subject to minimal training, and provides effective communication of relevant data while also communicating billing and timing information to associated billing programs and systems.

Figure 11:
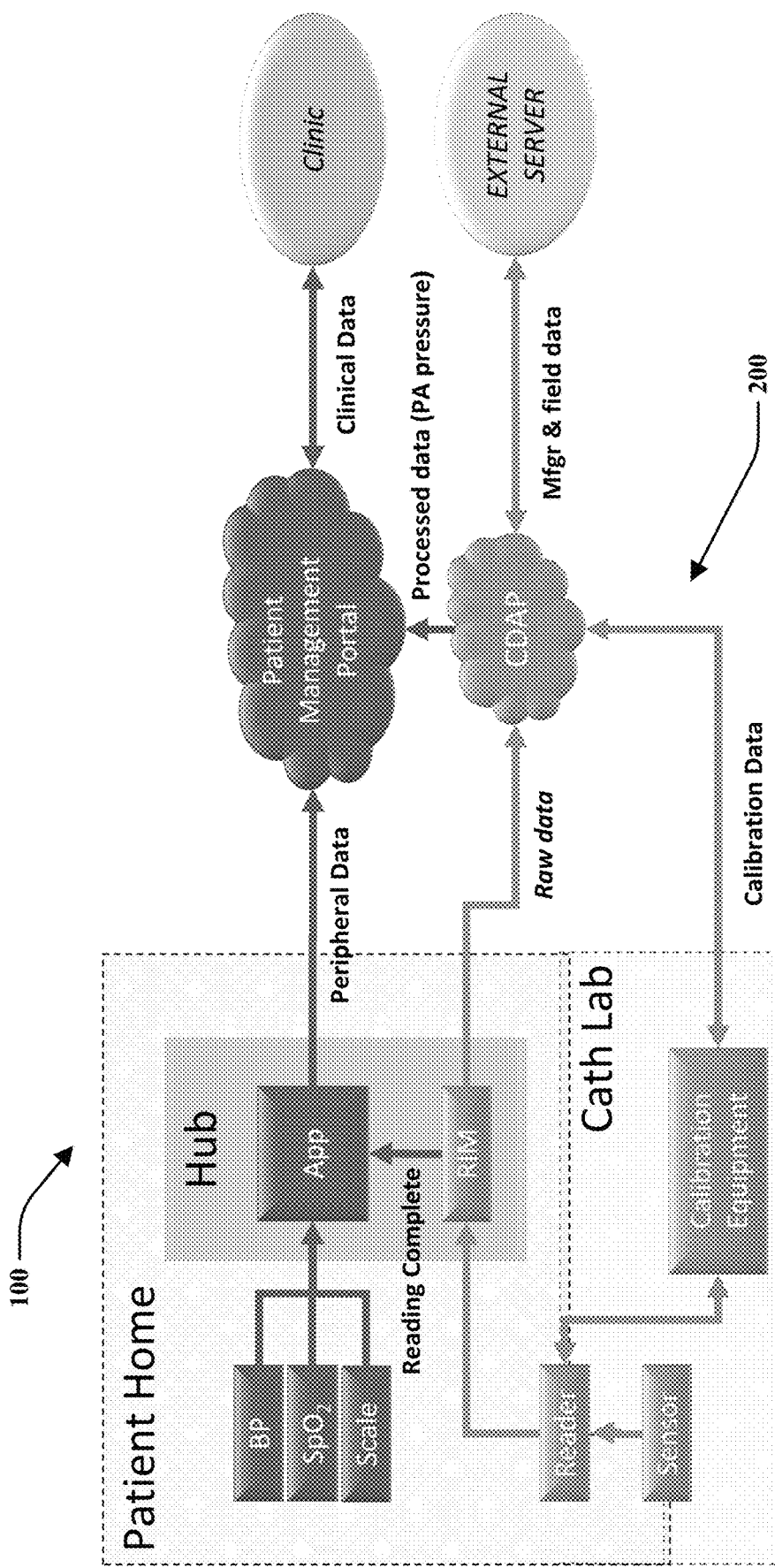
FIG. 11 illustrates a schematic flow chart illustrating features of the physiologic monitoring system of the instant application.

FIGS. 1, 2, and 11 illustrate that the management portal 130 may also include or communicate with the data analysis platform 132, referred to herein as the Cordella™ Data Analysis Platform (CDAP) 132. The CDAP may be a subsystem to the management portal 130. The CDAP 132 may be a program stored on a computer readable medium that is configured to communicate with the CorPASS system 200 or other invasive peripheral system or device 110B and in particular the RIM 128 of the CorPASS system 200. Alternatively, the CDAP 132 may be a web based application or a database designed for artificial intelligence or machine learning. In one embodiment, the CDAP 132 may function separately from the management portal 130 and the patient application 126 of the central hub 120 but may communicate information to the management portal 130 and may be stored on an external server. The interaction between the management portal 130 and the CDAP 132 includes separate functionality as the management portal 130 is designed to communicate with and display information monitored from non-invasive peripheral devices 110A while the CDAP 132 is designed to communicate with and display information from invasive peripheral devices 110B. The separate functionality may exist within the management portal 130 such that the portal 130 may be scalable to function with only non-invasive peripheral devices 110A, with only the invasive peripheral devices 110B, or with both devices 110A, 110B. The CDAP 132 may interface with calibration equipment such as the docking station 160, may store sensor calibration data, as well as sensor and reader factory settings. The CDAP 132 may process physiologic data monitored by the reader 150 and convert raw data such as frequency readings to processed data such as pulmonary artery pressure measurements. The CDAP 132 may communicate the processed data such as pulmonary artery pressure measurements to the management portal 130. The CDAP 132 may interface with the RIM 128, calibration equipment 160, and central hub 120 and may also be in communication with an external server to communicate manufacture and field related data. The CDAP 132 may also allow for machine learning of physiologic and/or other data. Additionally, the RIM 128 and the CDAP 132 may interface with at least one of the following invasive peripheral devices 110B including an implantable sensor, an actuator, a dialysis assembly, a drug delivery device, an infusion pump, a neuro-stimulation assembly, an oxygen delivery system, and a ventricular assistance device.

Turning to FIG. 2, the RIM 128 and CDAP 132 may be subsystems to or communicate with the central hub 120 and management portal 130 respectively. It is illustrated that the physiological monitoring system 100 and the CorPASS 200 may operate separately or may be integrated to allow collected physiologic data from each peripheral devices 110A and 110B to be analyzed and displayed by respective graphic user displays of the central hub 120 and management portal 130.

Figure 9:
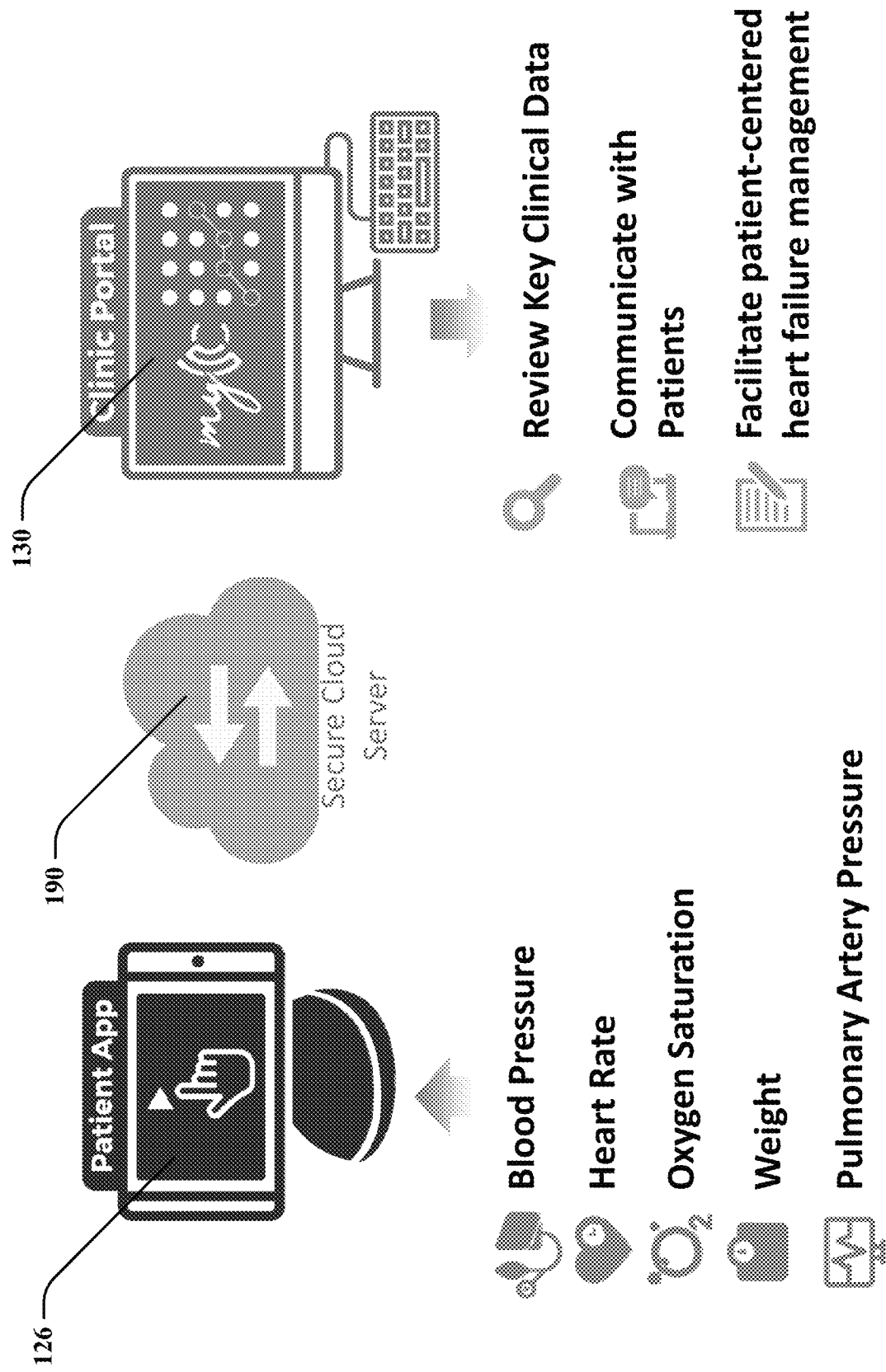
FIG. 9 illustrates a diagram of the function of the physiological monitoring system.

As illustrated by FIG. 9, the patient app 126 may display various types of physiologic or biometric data including data representative of blood pressure, heart rate, oxygen saturation, weight, and pulmonary artery pressure. This information may be displayed on the graphical user display 124. Additionally, the management portal 130 may be configured to allow a clinician to review key clinical data (representative of the measured physiologic data), communicate with patients through the patient application 126, and facilitate patient centered heart failure management. In this embodiment, the patient application 126 communicates with the management portal 130 through a secure cloud server 190.

Figure 10:
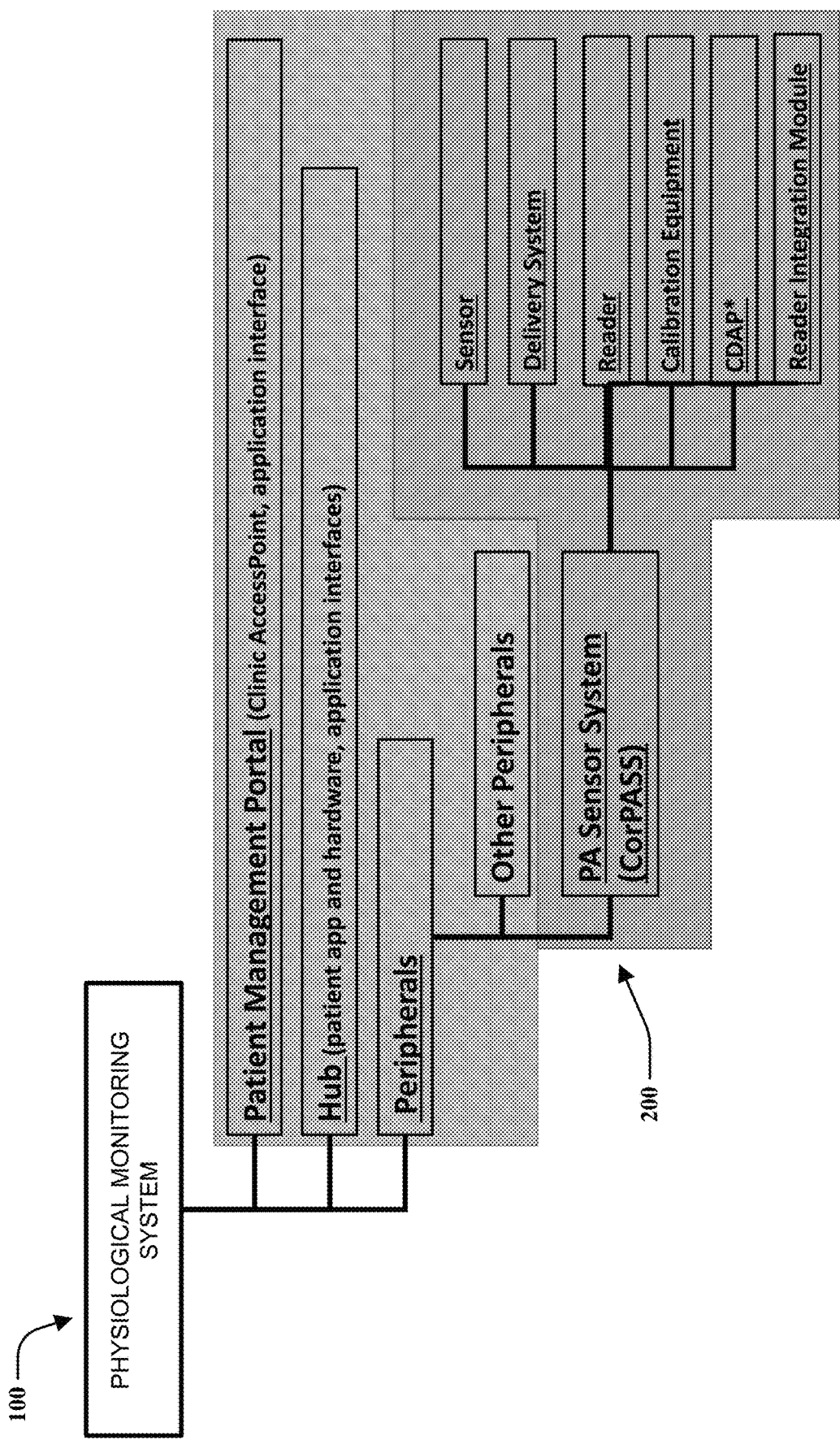
FIG. 10 illustrates a diagram of the physiologic monitoring system of the instant application.

FIG. 10 illustrates a hierarchical flow chart of the physiological monitoring system 100. This chart illustrates that the CorPASS system 200, which may include a sensor, delivery system, reader, calibration equipment, CDAP, and reader integration module (RIM), interfaces with the other peripheral devices 110A while being configured to communicate with the central hub 120 and management portal 130. The system is designed to be in compliance with US federal regulations including 21 CFR 820.30—Medical Device Design Controls and ISO 13485:2007/EN-ISO 13485:2016.

Stated another way, the system 100 may be described as the Cordella Heart Failure System which collects, records, and transmits physiologic data and communications from the patient at home to clinician(s) for assessment, patient communication, and patient-centered heart failure management. The system 100 includes at least the following components:

1. myCordella Patient Management Portal: 130 a clinic facing, web-based application which aggregates and displays the health status of patients, including biometric data and responses to health-related questions transmitted from the myCordella Hub 120 in the patient's home. The streamlined workflow defined by the Portal 130 enables clinicians to efficiently and effectively review patients; record notes and actions taken based on data trends; communicate with the patient and other clinicians regarding the patient's health status, and; provide supporting documentation for the clinician's continued, proactive management of the patient.
2. myCordella Hub: 120 an intuitive, patient-facing, device with a standalone application that reminds the patient daily to obtain physiologic measurements and respond to health-related questions; instructs the patient on proper collection of biometric data; aggregates collected data to provide a snapshot of the patient's health status, and; securely transmits the patient's current health status to the myCordella Patient Management Portal 130.
3. myCordella Peripherals: 110A medical or consumer health devices that collect biometric data (e.g. blood pressure, heart rate, blood oxygen and weight) and communicate with the myCordella Hub 120 to transmit data unaltered for display in the myCordella Patient Management Portal 130.
4. Cordella Pulmonary Artery Sensor System (CorPASS): 110B, 200 an innovative myCordella Peripheral designed for on-demand measurement of pulmonary artery pressure from the patient's home or elsewhere (to identify pulmonary congestion suggestive of worsening heart failure through trends in pulmonary artery pressures). The Cordella PA Sensor System includes: a catheter-based Delivery System 170 with a pre-loaded Sensor 180 for implant; Calibration Equipment 160 for collecting relevant calibration information during implantation; a myCordella Patient Reader 150 which enables patients to measure PA pressure at home from the sensor 180 implanted within the patient; and a cloud-based data analysis platform to store and analyze home PA pressure readings. Pulmonary artery pressure data is collected from the Cordella Sensor with the myCordella Patient Reader by the patient at home. The Reader uploads its data through the Reader Interface Module on the myCordella Hub to the data analysis platform where the analyzed data is shared with the myCordella Patient Management Portal 130, enabling a more complete picture of the health status of the patient(s).

When used together the components of the Cordella Heart Failure System 100 enable proactive, patient-centered heart failure management. FIG. 11 schematizes the Cordella subsystems and the data flow between them.

The embodiments of this disclosure have been described above and, obviously, modifications and alternations will occur to others upon reading and understanding this specification. The claims as follows are intended to include all modifications and alterations insofar as they are within the scope of the claims or the equivalent thereof.

Having thus described the invention, we claim:

1. A physiologic monitoring system comprising:
   a central hub in communication with a management portal;
   at least one non-invasive peripheral device to measure physiologic data from a patient in communication with said central hub;
   wherein physiologic data measured from a patient with at least one non-invasive peripheral device is communicated to the management portal, wherein said physiologic data is used to determine whether to include an invasive peripheral device for use by said patient and in communication with said central hub; and an invasive peripheral system associated with said patient and in communication with said central hub, wherein said invasive peripheral system includes said invasive peripheral device that is an implantable sensor configured for wireless communication with a sensor reader, the sensor reader adapted to measure physiologic data from said implantable sensor placed within a cardiovascular system of said patient;

wherein the central hub includes a processor and computer readable media, wherein the processor is configured to read the computer readable media and the computer readable media comprises a patient application and a reader interface module wherein the patient application and the reader interface module comprise separate functionality as the patient application is configured to communicate with said at least one non-invasive peripheral device while the reader interface module only communicates with said invasive peripheral system, and wherein the central hub is scalable to collect data and communicate with the non-invasive peripheral device and the invasive peripheral system such that data from the non-invasive peripheral device and the invasive peripheral system are selectively communicated to the management portal.

2. The physiologic monitoring system of claim 1 wherein said at least one non-invasive peripheral device includes a blood pressure cuff, an oxygen sensor, a weight scale, and an ECG monitor.

3. The physiologic monitoring system of claim 1 wherein said invasive peripheral device further includes at least one of an actuator, a dialysis assembly, a drug delivery device, an infusion pump, a neuro-stimulation assembly, an oxygen delivery system, or a ventricular assistance device.

4. The physiologic monitoring system of claim 3 further comprising a docking station for the reader device.

5. The physiologic monitoring system of claim 1 wherein said central hub includes a graphical user interface for displaying the patient application.

6. The physiologic monitoring system of claim 1 wherein said management portal is in communication with a data analysis platform that is configured to receive data from the reader interface module, analyze the received data to generate processed data, and communicate the processed data to the management portal.

7. A method of monitoring physiologic data comprising:
measuring physiologic data from a patient with at least one non-invasive peripheral device wherein physiologic data measured from said patient with at least one non-invasive peripheral device is communicated to a management portal through a patient application provided on a central hub, wherein the central hub comprises a processor and computer readable media, the processor configured to read the computer readable media and the computer readable media comprises the patient application;

analyzing said communicated physiologic data to determine whether to include an invasive peripheral device for use by said patient wherein said invasive peripheral device includes an implantable sensor;

measuring physiologic data from said patient with said invasive peripheral device placed within a cardiovascular system of said patient with a sensor reader;

communicating measured physiologic data to a reader interface module of the computer readable media of the central hub, wherein the patient application and the reader interface module function separately such that the patient application is designed to communicate with said at least one non-invasive peripheral device while the reader interface module separately communicates with said sensor reader; and communicating said physiologic data to said management portal to display to a user.

8. The method of monitoring physiologic data of claim 7 further comprising generating a plurality of health-related questions by the central hub to be answered by the patient.

9. The method of monitoring physiologic data of claim 7 further comprising aggregating the physiologic data and displaying the physiologic data at the central hub.

10. The method of monitoring physiologic data of claim 7 further comprising aggregating the physiologic data and displaying the physiologic data at the management portal.

11. The method of monitoring physiologic data of claim 7 wherein said non-invasive peripheral device includes at least one of a blood pressure cuff, an oxygen sensor, a weight scale, and an ECG monitor.

12. The method of monitoring physiologic data of claim 7, further comprising communicating between said implantable sensor and said wireless sensor reader to measure physiologic data from said implantable sensor placed within a cardiovascular system of said patient.

13. The method of monitoring physiologic data of claim 7 further comprising communicating measured physiologic data from said invasive peripheral device to a data analysis platform from the reader interface module wherein said data analysis platform analyzes said measured physiologic data and generates processed data wherein said processed data is communicated to the management portal.

14. A physiologic monitoring system comprising:
a central hub in communication with a management portal, said central hub comprises a process, a computer readable media and a graphical user interface for displaying a patient application, wherein the processor is configured to read the computer readable media and the computer readable media comprises the patient application and a reader interface module;

at least one non-invasive peripheral device to measure physiologic data from a patient in communication with said central hub, wherein physiologic data measured from said patient with at least one non-invasive peripheral device is communicated to said management portal through said patient application wherein said communicated physiologic data is used to determine whether to include an invasive peripheral device for use by said patient;

a peripheral system that includes said invasive peripheral device wherein said invasive peripheral device includes an implantable sensor and a sensor reader adapted to measure physiologic data from said implantable sensor placed within a cardiovascular system of said patient and in communication with said reader interface module of said central hub, wherein the patient application and the reader interface module include separate functionality as the patient application is designed to communicate with said at least one non-invasive peripheral device while the reader interface module separately communicates with said sensor reader;

wherein the central hub is scalable to collect and communicate measurements from the non-invasive peripheral device and the invasive peripheral device such that the central hub is scalable to function with only non-invasive peripheral devices, with only the invasive peripheral devices, or with both non-invasive and invasive devices; and wherein said management portal is in communication with a data analysis platform configured to receive data from said reader interface module and display said data at the management portal.

15. The physiologic monitoring system of claim 14 wherein said at least one non-invasive peripheral device includes a blood pressure cuff, an oxygen sensor, a weight scale, and an ECG monitor.

16. The physiologic monitoring system of claim 14 wherein said data analysis platform is configured to interface with the peripheral system and the invasive peripheral device to calibrate said invasive peripheral device.

17. A method of monitoring physiologic data comprising:
measuring physiologic data from a patient with at least one non-invasive peripheral device, wherein said non-invasive peripheral device includes at least one of a blood pressure cuff, an oxygen sensor, a weight scale, and an ECG monitor;

communicating said physiologic data to a central hub, said central hub comprises a processor and a computer readable media, wherein the processor is configured to read the computer readable media and the computer readable media comprises a patient application and a reader interface module;

communicating said physiologic data to a management portal through the patient application to display to a user;

analyzing said communicated physiologic data to determine whether to include an invasive peripheral system for use by the patient wherein said invasive peripheral system comprises an implantable sensor and a sensor reader;

measuring physiologic data from said implantable sensor placed within a cardiovascular system of said patient with said sensor reader;

communicating said physiologic data to said reader interface module of said central hub; and communicating said physiologic data to said management portal to display thereon.

18. The method of monitoring physiologic data of claim 17 further comprising aggregating the physiologic data and displaying the physiologic data at the management portal.

* * * * *